United States Patent [19]

Zamba

[11] Patent Number: 5,163,937
[45] Date of Patent: Nov. 17, 1992

[54] WATERPROOF BODY FOR CAUTERY DEVICES

[75] Inventor: Gene Zamba, Brooklyn, Conn.

[73] Assignee: Transtech Scientific, Inc., Washington, D.C.

[21] Appl. No.: 470,364

[22] Filed: Jan. 25, 1990

[51] Int. Cl.⁵ .................................. A61B 17/36
[52] U.S. Cl. ........................ 606/30; 606/29; 219/240
[58] Field of Search .................. 606/27–31, 606/40, 41; 362/157, 158; 219/221–241

[56] References Cited

U.S. PATENT DOCUMENTS

| | | |
|---|---|---|
| 1,401,104 | 12/1921 | Kruesheld et al. |
| 1,677,209 | 7/1928 | Rose . |
| 1,717,480 | 6/1929 | Wappler . |
| 1,812,608 | 6/1931 | Roberts . |
| 2,030,285 | 2/1936 | Dinyer ............................ 219/31 |
| 3,234,356 | 2/1966 | Babb ............................... 219/233 |
| 3,336,916 | 8/1967 | Edlich .............................. 128/2 |
| 3,460,539 | 8/1969 | Anhalt ........................ 128/303.17 |
| 3,461,874 | 8/1969 | Martinez ..................... 128/303.17 |
| 3,613,682 | 10/1971 | Naylor ............................. 606/30 |
| 3,662,151 | 5/1972 | Haffey ............................ 219/233 |
| 3,720,896 | 3/1973 | Beierlein ......................... 335/206 |
| 3,723,704 | 3/1973 | Silverthorne .................... 219/242 |
| 3,886,944 | 6/1975 | Jamshidi ....................... 128/303.1 |
| 3,906,955 | 9/1975 | Roberts ....................... 128/303.1 |
| 3,974,833 | 8/1976 | Durden ........................ 128/275.1 |
| 3,978,312 | 8/1976 | Barton et al. ..................... 606/30 |
| 4,016,881 | 4/1977 | Rioux et al. .................. 128/303.17 |
| 4,034,762 | 7/1977 | Cosens et al. ................ 128/303.17 |
| 4,074,110 | 2/1978 | Slaughter ......................... 219/240 |
| 4,108,181 | 8/1978 | Saliaris ........................ 128/303.1 |
| 4,301,802 | 11/1981 | Poler .......................... 128/303.14 |
| 4,359,052 | 11/1982 | Staub .......................... 128/303.1 |
| 4,418,692 | 12/1983 | Guay .......................... 128/303.14 |
| 4,463,759 | 8/1984 | Garito et al. ................ 128/303.14 |
| 4,492,231 | 1/1985 | Auth ........................... 128/303.17 |
| 4,563,570 | 1/1985 | Johns .............................. 606/30 |
| 4,606,342 | 2/1985 | Zamba et al. .................... 606/30 |
| 4,655,215 | 4/1987 | Pike ........................... 128/303.14 |
| 4,708,136 | 11/1987 | Saito ........................... 128/303.1 |

FOREIGN PATENT DOCUMENTS

| | | |
|---|---|---|
| 2504508 | 8/1976 | Fed. Rep. of Germany . |
| 2573301 | 5/1986 | France . |
| 1564435 | 4/1980 | United Kingdom . |

Primary Examiner—Stephen C. Pellegrino
Assistant Examiner—Steven J. Shumaker
Attorney, Agent, or Firm—Stephen Glazier

[57] ABSTRACT

A waterproof body for an electric cautery containing cautery parts, comprising a cautery tip assembly, a first hollow half body with a button hole in its side and a receptacle in one end so as to receive the cautery tip assembly, a second hollow half body with a receptacle in on end to receive the cautery tip assembly, a waterproof flexible membrane fastened to the inside of the first half body so as to seal the button hole in a waterproof manner, and an electrical switch button fastened in the button hole of the first half body. The first and second half bodies are joined together in a waterproof manner by ultrasonic welding. The electrical switch button slides in an axial manner relative to the body.

13 Claims, 2 Drawing Sheets

WATERPROOF BODY FOR CAUTERY DEVICES

BACKGROUND OF THE INVENTION

This invention relates generally to a waterproof body for cautery devices, and a method for assembling the same. More specifically this invention relates to a waterproof, disposable, non-reusable cautery body for hand-held cautery devices of either the fixed temperature variety or the variable temperature variety.

A cautery is a commonly used medical device with a hand-held component with a wire loop at its tip end. Electricity is run through the wire tips causing the tip to be hot. The hot tip is used to seal small blood vessels that are cut in the process of surgery. Permanent re-usable cauteries have a hand-held component which is connected by an electric cord to a permanent electric power source.

Hand-held disposable cauteries generally have body parts made of PVC plastic, and are powered by conventional dry cell batteries contained within the body of the hand-held disposable cautery. Depending on size, either AA size or AAA size batteries are most commonly used, providing direct current. Other parts, such as electrical connectors, a spring compressing the batteries, and a switch are also contained within the disposable cauteries. In the case of a single temperature cautery, an on/off switch activated by depressing a button in the cautery is usually used. In the case of a variable temperature cautery, a rheostat variable resistor switch is often used, activated and adjusted by a sliding button in the body of the cautery. These hand-held disposable cauteries are made much like a penlight, except the cauteries have a hot wire tip in place of a light bulb.

U.S. Pat. No. 3,613,682 issued to Naylor on Oct. 19, 1971 teaches a disposable hand-held cautery operated by internal batteries, much in the manner of a penlight.

U.S. Pat. No. 4,606,342, issued to Eugene Zamba and Lynan Zamba, on Feb. 15, 1985, teaches a hand-held disposable cauterizing device with a variable temperature cautery tip.

Disposable cauteries have developed a multitude of other nonmedical uses due to their portable nature and their relatively inexpensive cost, including use for clipping dog and cat claws, and repair of fly fishing lures that are damaged on location at fishing sites. Further, disposable hand-held cauteries have made cauteries available in medical situations, such as emergency sites, where electricity is not available.

Prior art of disposable cauteries has demonstrated several problems that have limited the utility and market for disposable cauteries. Indeed, the variable temperature disposable cautery has not even entered production yet, in part because of such problems. These problems are addressed by the present invention. The existing problems include: a shortened shelf life in wet or humid conditions (because humidity and water undermine the life of the batteries that are installed in the cauteries when they are made); a tendency for the disposable cauteries to short out and lose their function when submerged in blood or other fluids in the surgical field; unhygienic conditions caused by the device when blood and other body fluids enter the body of the device around the on/off button; an inability to properly clean the device for re-use once blood and other body fluids have entered into the internal portions of the device; a tendency by some medical users to attempt to re-sterilize and re-use the device (under conditions where effective sterilization is impossible); and an inability to fully exploit the devices in emergency or primitive medical situations since contact with wet or humid conditions tend to deactivate and destroy the device when water contacts the batteries.

SUMMARY OF THE INVENTION

The present invention is a waterproof body for a disposable, handheld battery-operated electric cautery, with internally held batteries. A variation of the present invention has a feature that discourages attempts to sterilize and reuse the device.

Basically, the present invention consists of a cylindrical plastic body made from two longitudinally divided halves. When the two body halves are assembled, there is a hole in one end of the body that allows the insertion of the cautery tip, which tip has a plastic rim. One half of the cautery body has a hole in its side that permits insertion of a button to turn the cautery on and off, and to vary its temperature in the variable temperature model. A flexible membrane is fastened to the inside of the body, over the hole for the on/off button, that prevents water and humidity from entering the body around the button. The seams of the assembled cautery between the cautery tip and the two body halves are sealed in a waterproof manner by using ultrasound welding of the plastic parts upon assembly. The two half body parts, the button and the rim of the cautery tip are plastic.

A non-sterilizable version of the cautery uses a plug in the end of the cylindrical body opposite from the cautery tip. The plug is made of dimensions so that it inserts in a waterproof tight fit in the end of the body at normal room temperature. The plug however is made of a memory plastic polymer. When the plug is heated to temperatures necessary for sterilization, the plug reduces its diameter so it fits loosely in the cautery body and is ejected from the cautery body by the springs in the cautery used in relation to the batteries. In effect then when the cautery is heated in an attempt to re-sterilize it for re-use, the device pops apart and is rendered dysfunctional.

The present invention's method of assembly of the device involves first ultrasonically welding the waterproof membrane over the button hole in one half of the cautery body. The internal parts of the cautery are then assembled into the cautery body, including the batteries, electrical contacts, wiring, a switch and springs commonly used in the field. The two halves of the body and the cautery tip are then assembled and the seams between these parts are ultrasonically welded to be waterproof. In the case where the memory plastic plug is used, the plug is then inserted into the end of the body in a watertight manner without ultrasonic welding. The button is then press fitted into the button hole exterior to the membrane and is press fitted over the flexible membrane onto the on/off switch components or the variable rheostat switch components inside the membrane. The membrane is flexible enough to maintain its watertight capacity when the button is depressed in the on/off mode or when slid axially along the body to vary the temperature in the variable temperature cautery.

The membrane may be made out of latex. The body parts, button, rim of the cautery tip, and the plug are best made by injection molding of plastic, and except for the plug, PVC plastic may be the best material for manufacture. Although automatic assembly of the present invention is possible, economics often require manual assembly. Where medical applications require, the assembled cautery can be sterilized and sterile-wrapped in individual units for shipment prior to use.

DESCRIPTION OF PREFERRED EMBODIMENTS

Figures 1, 1A:
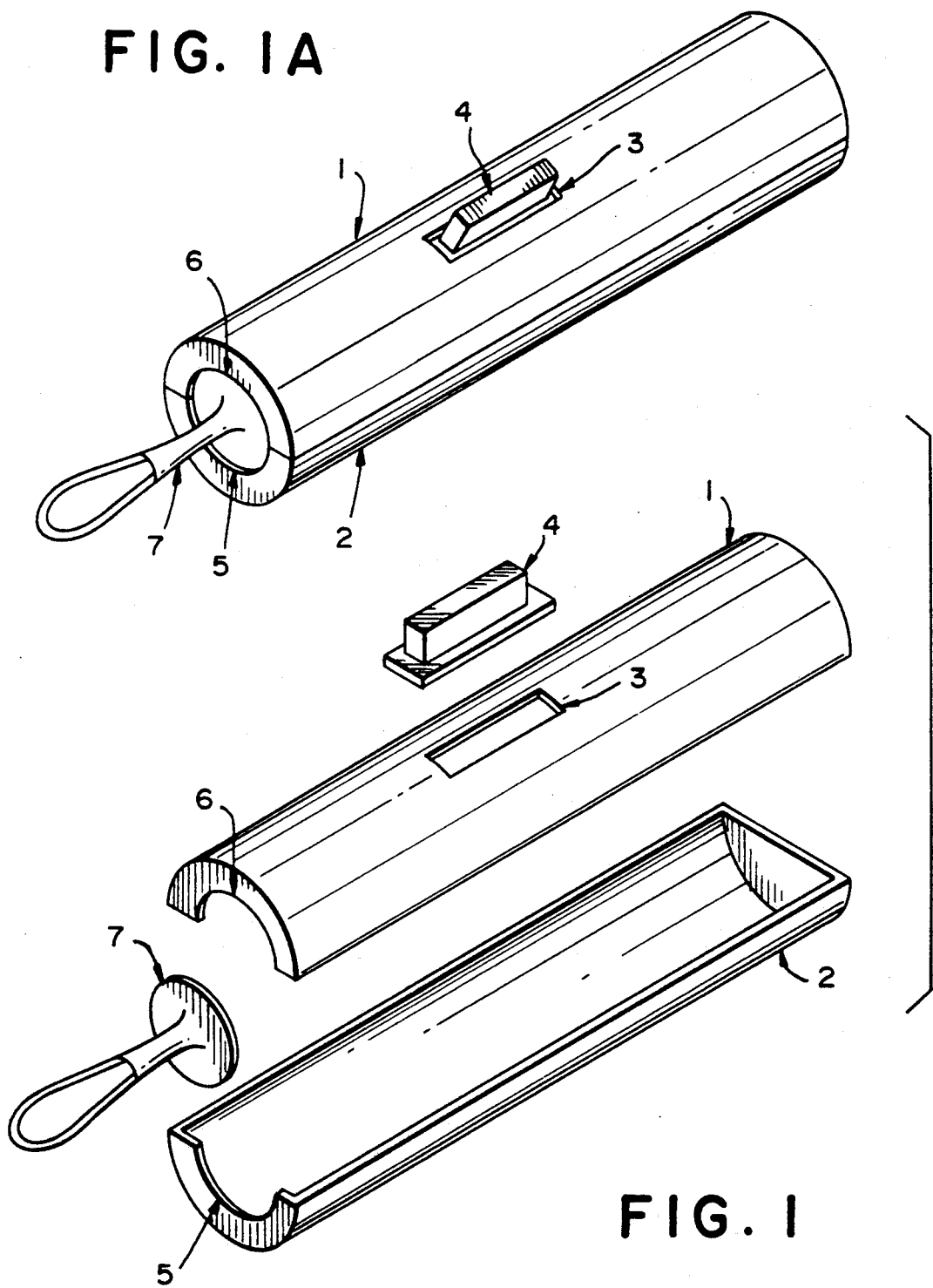
FIG. 1 is an exploded drawing of the waterproof cautery body showing the external body parts, not including the membrane or the end-plug.
FIG. 1A is an assembled view of the same parts shown in FIG. 1 in exploded view.

FIG. 1 shows, in exploded mode, the cautery body comprising a body half 1 with a button hole 3 and a receptacle 6 for the cautery tip 7, a body half 2 with no button hole, a receptacle 5 for the cautery tip 7, and a snap in on/off button 4. FIG. 1 does not show flexible membrane 11, which is shown in FIGS. 2 and 3.

FIG. 1A is an assembled view of the same parts as shown in exploded mode in FIG. 1.

Figure 2:
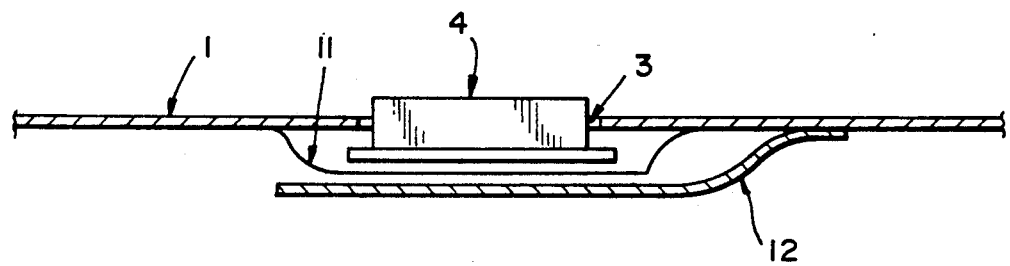
FIG. 2 is a cross-sectional view showing the insertion of the on/off button in the single temperature cautery with the waterproof membrane around the button hole and the electrical connector means serving as a switch apparatus inside the cautery.

FIG. 2 shows a cross sectional view of the side of the cautery body half 1 with the button hole 3 and the snapped in button 4 and the flexible waterproof membrane 11 ultrasonically welded to the interior of the body half 1, and the electrical connector 12 serving as a switch means attached to the inside of the body half 1.

Figure 3:
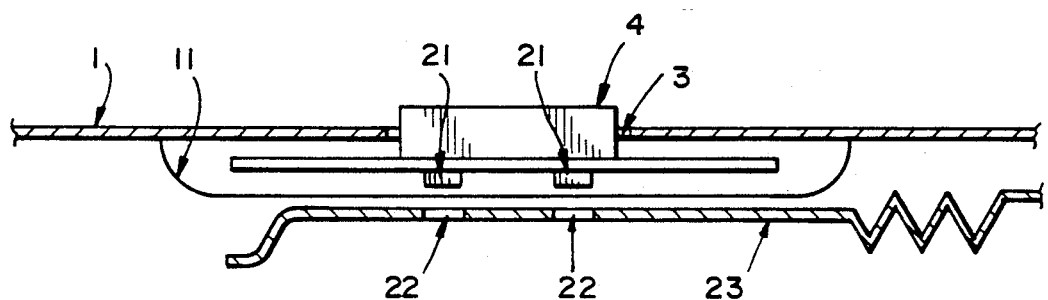
FIG. 3 is a cross sectional view similar to FIG. 2, showing the parts around the temperature variance button in the variable temperature cautery, which uses a longitudinally sliding button.

FIG. 3 is a cross section view regarding the variable temperature cautery, comprising the cautery half 1 with the button hole 3, the snap in variable temperature button 4, the flexible waterproof membrane 11, the snap fit tips 21 of the button 4, and the snap fit hole receptacles 22 in the electrical connector 23 to receive snapfit tips 21.

Figure 4:
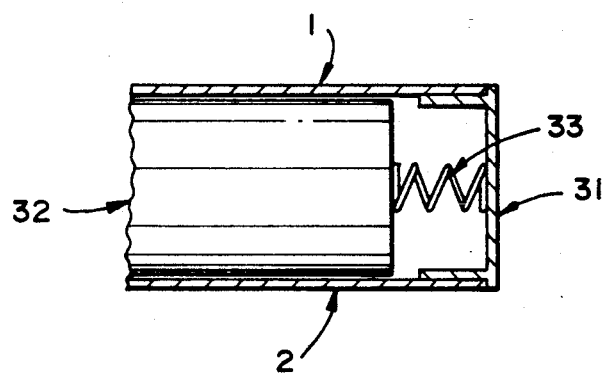
FIG. 4 is a cross-sectional view showing the pop-out end-plug in the end of the cautery body opposite the wire cautery tip, which plug pops out when the cautery is heated to be re-sterilized for attempted re-use.

FIG. 4 shows the cross sectional view of the body half 1, and the body half 2, and the memory plastic pop out plug 31 inserted into the assembled two body halves 1 and 2, with the internally held battery 32 and the spring 33 in compression when assembled between battery 32 and plug 31.

The embodiments as illustrated and discussed in this specification are intended only to teach those skilled in the art the best way known by the inventor to make and use the invention. Nothing in the specification should be considered as limiting the scope of the present invention. Many changes could be made by those skilled in the art to produce equivalent systems without departing from the invention. The present invention should be limited only by the following claims and their legal equivalents.

I claim:

1. A waterproof body for an electric cautery, containing cautery parts, comprising:

a first hollow half body with a button hole in its side said first half body having a receptacle in one end, said cautery tip assembly received in said receptacle;

a second hollow half body with a receptacle in one end, said cautery tip assembly received in said receptacle, said first and second half bodies being joined together;

a waterproof flexible membrane fastened to the inside of said first half body so as to seal said button hole in a waterproof manner;

an electrical switch button fastened in said button hole of said first half body;

a source of electrical power;

an electrical switch contained within said first and second bodies and engaged by said electrical switch button; and an electrical conducting means contained inside said first and second bodies electrically connecting said electrical conductor of said cautery tip assembly, said source of electrical power, and said electrical switch.

2. A waterproof battery-operated electric cautery comprising:

a cautery tip assembly;

a first hollow half body with a button hole in its side said first half body having a receptacle in one end, said cautery tip assembly received in said receptacle;

a second hollow half body with a receptacle in one end, said cautery tip assembly received in said receptacle, said first and second half bodies being joined together;

a waterproof flexible membrane fastened to the inside of said first half body so as to seal said button hole in a waterproof manner;

an electrical switch button fastened in said button hole of said first half body;

a number of electrical batteries contained inside said body;

an electrical switch contained inside said first and second bodies and engaged by said electrical switch button; and, an electrical conducting means contained inside said first and second bodies electrically connecting said electrical conductor of said cautery tip assembly, said number of electrical batteries, and said electrical switch.

3. The body in claim 2, said membrane comprised of a latex material.

4. The body in claim 2 where the said electrical switch button is slidably fitted in said button hole, said electrical switch button sliding in an axial manner relative to said body.

5. The body in claim 2, each of said first and second half bodies having a receptacle in the end of the body opposite said cautery tip assembly, and a plug waterproofed and inserted into said receptacle.

6. The body in claim 5 wherein said plug is comprised of a memory material which contracts when heated so as to cause a loose fit in said receptacle for said plug.

7. The body in claim 2 wherein said first and second half bodies, said cautery tip assembly, and said membrane are sealed together in a waterproof manner so as to form a single waterproof body.

8. The body in claim 7, said first half body, said second half body said non-conductive housing of said cautery tip assembly, and said membrane being comprised of plastic materials.

9. The body in claim 8, said first and second half bodies, said cautery tip assembly, and said membrane being ultrasonically welded together so as to form a waterproof seal.

10. The cautery in claim 2 where said electrical switch has a first on position, and a second off position.

11. The cautery in claim 10 where said electrical switch is a rheostat switch having a sliding spectrum of positions ranging from the off position to the full power position, in a series of increasing power.

12. A method of assembling a body for an electric cautery comprising the steps of:

attaching a flexible membrane in a waterproof manner to the interior of a first half body, said first half body having a button hole;

positioning the cautery components on the interior of said first half body;

attaching a second half body and a cautery tip to said first half body;

sealing said cautery tip, said first and second half bodies together;

inserting a snap-fit electrical switch button into said button hole of first said half body; and fitting said snap-fit button adjacent an internal switch in the assembled cautery tip, said first half body and said second half body.

13. The method of claim 12, said step of sealing being by ultrasonic welding.

* * * * *